United States Patent [19]

Vesperini et al.

[11] Patent Number: 5,306,498
[45] Date of Patent: Apr. 26, 1994

[54] COSMETIC COMPOSITION IN THE FORM OF A TRIPLE EMULSION

[75] Inventors: Laurence Vesperini, Paris; Pierre Fodor, Garches; Françoise Bouget, Fontenay-sous-Bois, all of France

[73] Assignee: L'Oreal, Paris, France

[21] Appl. No.: 862,716

[22] Filed: Apr. 3, 1992

[30] Foreign Application Priority Data

Apr. 5, 1991 [FR] France ................... 91 04209

[51] Int. Cl.⁵ ............... A61K 9/113; A61K 7/00
[52] U.S. Cl. .................... 424/401; 424/63; 424/64; 424/60; 514/847; 514/772.4; 514/937
[58] Field of Search ........... 424/63, 64, 401, 60; 514/847, 772.4, 937

[56] References Cited

U.S. PATENT DOCUMENTS

| | | | |
|---|---|---|---|
| 4,714,566 | 12/1987 | Takahashi et al. | 252/314 |
| 4,803,067 | 2/1989 | Brunetta et al. | 424/63 |
| 4,837,019 | 6/1989 | Georgalas et al. | 424/60 |
| 4,863,725 | 9/1989 | Deckner et al. | 514/772.4 |
| 4,946,832 | 8/1990 | Goode et al. | 514/937 |
| 4,960,764 | 10/1990 | Figueroa, Jr. et al. | 514/939 |
| 4,973,473 | 11/1990 | Schneider et al. | 514/847 |

FOREIGN PATENT DOCUMENTS

| | | |
|---|---|---|
| 0345075 | 12/1989 | European Pat. Off. . |
| 0360292 | 3/1990 | European Pat. Off. . |
| 2165163 | 10/1985 | United Kingdom . |
| 9100106 | 1/1991 | World Int. Prop. O. . |

OTHER PUBLICATIONS

Creams & Lotions Documentary: "Three-Phase Emulsions: Perfluoropolyether-Oil-Water", vol. 101, Nov. 1986, Baden et al.

Rohstoffe Werkstoffe Hilfsstoffe-"Emulsifiers A Novel Emulsification Technique of Perfluoropolyethers" No. 14 Sep. 3, 1990.

*Primary Examiner*—Thurman K. Page
*Assistant Examiner*—James M. Spear
*Attorney, Agent, or Firm*—Cushman, Darby & Cushman

[57] ABSTRACT

The invention relates to a triple emulsion comprising:
(A) a continuous gelled outer aqueous phase, containing, as gelling agent, at least one acrylic or methacrylic acid polymer or copolymer, combined with a polyglyceryl methacrylate;
(B) a fatty phase dispersed in the outer aqueous phase, and an aqueous phase (C) dispersed in the fatty phase. Process for preparing a triple emulsion conforming to the invention.

Application in cosmetics and dermatology.

23 Claims, No Drawings

COSMETIC COMPOSITION IN THE FORM OF A TRIPLE EMULSION

The present invention relates to cosmetic compositions provided in the form of a triple emulsion, to the process for producing these and to their applications in the cosmetology field.

Emulsions have for many years been used in cosmetics, especially in products for the cosmetic treatment of the skin. These emulsions are generally oil-in-water or water-in-oil emulsions (O/W) or (W/O).

Triple emulsions W/O/W or O/W/O have already been described in the state of the art. However, such emulsions have many problems both with respect to their production and with respect to their stability over time especially when these incorporate active substances which tend to destabilize them.

The Applicants have discovered, and this constitutes the subject of the invention, a triple emulsion exhibiting characteristics of stability and cosmetic feel which are particularly remarkable, and comprising a continuous gelled outer aqueous phase, a fatty phase dispersed in the outer aqueous phase and an inner aqueous phase dispersed in the said fatty phase. This triple emulsion in particular enables cosmetic or dermatological active substances to be incorporated in greater quantities compared with those which could possibly be introduced in emulsions of the state of the art without destabilizing the emulsion as a result.

The subject of the invention is therefore a triple emulsion exhibiting the characteristics defined below.

Another subject of the invention is the process for producing such an emulsion.

The subject of the invention is also the cosmetic application of such emulsions.

Other subjects of the invention will emerge on reading the following description and examples.

The triple emulsion conforming to the invention is essentially characterized in that it comprises (A) a continuous gelled outer aqueous phase, containing, as gelling agent, at least one acrylic or methacrylic acid polymer or copolymer, combined with a polyglyceryl methacrylate; (B) a fatty phase dispersed in the outer aqueous phase and an aqueous phase (C) dispersed in the fatty phase.

In accordance with a preferred embodiment of the invention, the gelled outer aqueous phase represents 40 to 60% by weight of the total emulsion, the fatty phase representing 10 to 25% of the total emulsion.

According to a preferred embodiment of the invention, a combination of two gelling agents are used in the outer aqueous phase consisting, on the one hand, of an alkali metal salt of an acrylic copolymer sold under the name HOSTACERINE PN 73 by HOECHST and, on the other hand, of a polyglyceryl methacrylate produced under the name LUBRAGEL MS by UNITED GUARDIAN INC.

The fatty phase comprises, in particular, vegetable oils, mineral or synthetic oils. Waxes and/or silicone oils may also be introduced into this fatty phase.

A preferred embodiment consists in the use, in the fatty phase, of a perfluorinated oil, in particular a perfluoropolyether of the formula:

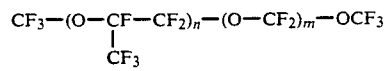

$$CF_3-(O-CF-CF_2)_n-(O-CF_2)_m-OCF_3$$
$$|$$
$$CF_3$$

in which n and m are integers such that the molecular weight is between 100 and 10,000, the n/m ratio being between 20 and 40.

The products which can be used in particular within the framework of the invention consist of the products sold under the name FOMBLIN HC, sold and produced by MONTEFLUOS, Milan, Italy, and in particular the products FOMBLIN HC/04, FOMBLIN HC/25, and FOMBLIN HC/R.

The triple emulsion conforming to the invention contains one or more active substances in proportions which may be as high as 20% by weight relative to the weight of the total emulsion. These active substances may consist in particular of UV-A, UV-B or broad band sunscreen agents, of natural protein extracts such as collagen-based products, preferably of marine origin.

The triple emulsions contain, in addition, emulsifiers used in the preparation of water-in-oil (W/O) and oil-in-water (O/W) emulsions.

According to a preferred embodiment of the process of the invention, in a first stage, a W/O emulsion is prepared by adding an aqueous phase to the fatty phase so as to obtain a W/O emulsion followed, in a second stage, by the preparation of the triple emulsion by adding the W/O emulsion thus obtained to a second gelled aqueous phase which constitutes the outer aqueous phase of the emulsion.

The emulsifier used for preparing the W/O emulsion preferably comprises a sorbitan oleate, lecithin mixture and, as co-emulsifier, a dodecyl glycol and ethylene oxide copolymer, such as more particularly the product sold under the name ELFACOS ST37 by AKZO.

The second gelled aqueous phase comprises an emulsifier chosen preferably from sucrose esters.

The addition of the active substances and the usual adjuvants such as perfumes, preservatives, may be carried out after preparation of the triple emulsion.

The gelling agents used in the outer aqueous phase generally represent 0.1 to 4.0% by weight relative to the total weight of the triple emulsion, and preferably 0.2 to 2.5% by weight.

Lecithin/oleate weight ratios of between about 4/2 and 8/2, and preferably equal to about 5/2 and copolymer/oleate co-emulsifier weight ratios of between 0.2/2 and ½ and preferably equal to 0.375/2, may be envisaged in the compositions in the form of an emulsion according to the invention.

As already indicated above, the compositions in the form of triple emulsions conforming to the invention exhibit particularly remarkable cosmetic properties, in particular with respect to the feel, which makes it possible to use them as foundations for applying active cosmetic substances to the skin.

These emulsions exhibit, in addition, stability characteristics which are perfectly acceptable under the usual conditions for storing cosmetic products.

These emulsions may in particular be used in protective creams, in so-called "barrier" creams, or alternatively in compositions for preventing skin irritations. They may be used in products for the cosmetic treatment of keratinous materials, such as various creams for anti-sun products, foundations, day creams, and the like.

These emulsions may also be used in dermatological applications as carriers for active agents used in dermatology.

The following example is intended to illustrate the invention without being limiting as a result.

EXAMPLE

| FATTY PHASE (B) | |
| --- | --- |
| Octyl palmitate | 7.00% |
| Karite butter | 1.50 |
| Block copolymer containing 22 ethylene oxide units and 9 dodecyl glycol units (ELFACOS ST 37) | 0.20 |
| Dimethicone (polydimethylsiloxane) | 3.00 |
| Perfluoropolymethylisopropylether (FOMBLIN HC/25) | 1.00 |
| Sorbitan oleate (SPAN 80 sold by ICI) | 2.00 |
| Natural hydrogenated lecithin | 5.00 |
| Tocopherol | 0.20 |
| 2-ethylhexyl Para-methoxycinnamate (PARSOL MCX sold by GIVAUDAN) | 0.50 |
| Propyl para-hydroxybenzoate | 0.10 |
| AQUEOUS PHASE I (C) | |
| Potassium sorbate | 0.10 |
| Water | 20.00 |
| Hydrolyzed animal protein | 10.00 |
| AQUEOUS PHASE II (A) | |
| Sodium acrylate/acrylamide copolymer (HOSTACERINE PN 73) | 0.25 |
| Polyglyceryl methacrylate (LUBRAGEL MS) | 2.00 |
| Methyl gluceth-20 sesquistearate | 1.50 |
| Glycerin | 4.00 |
| Methyl para-hydroxybenzoate | 0.25 |
| Water | 36.80 |

*CTFA Dictionary names.

The above triple emulsion is prepared in the following manner:

a) a W/O emulsion is prepared by adding, around 60° C., the aqueous phase C. to the fatty phase B under turbo stirring;

b) the W/O emulsion thus obtained is added to the second gelled aqueous phase A.

The following active substances and adjuvants are then added:

| Collagen | 2.00 |
| --- | --- |
| Perfume | 0.30 |
| Imidazolidinyl urea | 0.30 |
| Water | 2.00 |

We claim:

1. A water/oil/water triple emulsion comprising
(a) continuous gelled outer aqueous or water phase containing, as a gelling agent, at least one acrylic or methacrylic acid polymer or copolymer, combined with a polyglyceryl methacrylate;
(b) a fatty or oil phase dispersed in said outer aqueous phase; and
(c) an inner aqueous or water phase dispersed in said fatty or oil phase.

2. The triple emulsion of claim 1 wherein said gelled outer aqueous or water phase represents from 40 to 60 weight percent of the total triple emulsion and said fatty or oil phase represents from 10 to 25 weight percent of the total triple emulsion.

3. The triple emulsion of claim 1 wherein said gelling agent present in said gelled outer aqueous or water phase is an alkali metal salt of an acrylic copolymer combined with a polyglyceryl methacrylate.

4. The triple emulsion of claim 1 wherein said fatty or oil phase comprises a vegetable oil, a mineral oil or a synthetic oil.

5. The triple emulsion of claim 4 wherein said fatty or oil phase also contains at least one of a wax or a silicone oil or both.

6. The triple emulsion of claim 4 wherein said fatty or oil phase contains a perfluorinated oil.

7. The triple emulsion of claim 6 wherein said perfluorinated oil is a perfluoropolyether having the formula

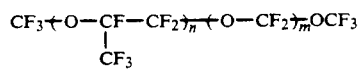

wherein n and m are integers such that the molecular weight ranges from 100 to 10,000 and wherein the ratio, n/m is between 20 and 40.

8. The triple emulsion of claim 1 wherein said fatty or oil phase contains a dedecyl glycol and ethylene oxide copolymer as a co-emulsifier.

9. The triple emulsion of claim 6 wherein said fatty or oil phase contains, in combination said perfluorinated oil, and a dodecylglycol and ethylene oxide copolymer as a co-emulsifier.

10. The triple emulsion of claim 1 wherein said gelling agent is present in an amount ranging from 0.1 to 4.0 percent by weight based on the total weight of said triple emulsion.

11. The triple emulsion of claim 1 wherein said gelling agent is present in an amount ranging from 0.2 to 2.5 percent by weight based on the total weight of said triple emulsion.

12. The triple emulsion of claim 1 wherein said fatty or oil phase contains sorbitan oleate and lecithin as emulsifiers wherein the lecithin/sorbitan oleate weight ratio is between 4/2 and 8/2.

13. The triple emulsion of claim 1 wherein said fatty or oil phase contains sorbitan oleate and lecithin as emulsifiers wherein the lecithin/sorbitan oleate weight ration is 5/2.

14. The triple emulsion of claim 1 wherein said gelled outer aqueous or water phase contains a sucrose ester as an emulsifier.

15. The triple emulsion of claim 1 which contains up to 20 percent by weight, based on the total weight of said emulsion, of a cosmetic or dermatologic active substance.

16. A process for preparing a water/oil/water triple emulsion comprising
(a) in a first stage preparing a water-in-oil emulsion by adding an aqueous or water phase to a fatty or oil phase so as to obtained said water-in-oil emulsion, and
(b) in a second stage, adding said water-in-oil emulsion prepared in stage (a) to a gelled aqueous or water phase containing, as a gelling agent, an acrylic or methacrylic acid polymer or copolymer combined with a polyglyceryl methacrylate so as to produce said triple emulsion.

17. The process of claim 16 which includes introducing a perfluorinated oil into said fatty or oil phase.

18. The process of claim 16 which includes introducing, as a co-emulsifier, a dodecyl glycol and ethylene oxide copolymer into said fatty or oil phase.

19. The process of claim 16 which includes introducing a perfluorinated oil, and a dodecyl glycol and ethylene oxide copolymer, as a co-emulsifier, into said fatty or oil phase.

20. The process of claim 16 which includes in said first stage (a) adding a mixture of sorbitan oleate and lecithin as an emulsifier in preparing said water-in-oil emulsion.

21. The process of claim 16 which includes in said second stage (b) adding a sucrose ester, as an emulsifier, to said gelled aqueous or water phase.

22. The process of claim 16 includes a third stage (c) comprising introducing at least one active substance into said triple emulsion prepared in step (b).

23. A composition for application to the skin comprising a water/oil/water triple emulsion defined in claim 1, said triple emulsion containing at least one cosmetically or dermatologically active agent.

* * * * *